(12) United States Patent
Ando

(10) Patent No.: US 8,338,503 B2
(45) Date of Patent: Dec. 25, 2012

(54) MOLDABLE RESIN FOR DENTAL USE

(76) Inventor: Hiroshi Ando, Nagoya (JP)

( * ) Notice: Subject to any disclaimer, the term of this patent is extended or adjusted under 35 U.S.C. 154(b) by 0 days.

(21) Appl. No.: 12/930,353

(22) Filed: Jan. 4, 2011

(65) Prior Publication Data

US 2011/0223565 A1    Sep. 15, 2011

(30) Foreign Application Priority Data

Mar. 10, 2010    (JP) ................................ 2010-053775

(51) Int. Cl.
    *A61K 6/083*      (2006.01)

(52) U.S. Cl. .............. 523/105; 523/115; 433/212.1; 433/218

(58) Field of Classification Search .......... 604/18, 604/15, 12, 13
See application file for complete search history.

(56) References Cited

U.S. PATENT DOCUMENTS

| | | | | |
|---|---|---|---|---|
| 4,211,682 A | 7/1980 | Suminoe | ...................... | 260/29.3 |
| 4,414,990 A | 11/1983 | Yost | ...................... | 132/91 |
| 5,366,505 A | 11/1994 | Faber | ...................... | 623/11 |
| 5,635,162 A | 6/1997 | Fischer | ...................... | 424/49 |
| 5,722,833 A | 3/1998 | Fischer | ...................... | 433/217.1 |
| 5,872,160 A | 2/1999 | Liang | ...................... | 528/120 |
| 5,877,232 A | 3/1999 | Storch | ...................... | 523/116 |
| 5,877,233 A | 3/1999 | Liang | ...................... | 523/120 |
| 5,967,155 A | 10/1999 | Marcon | ...................... | 132/321 |
| 6,069,188 A | 5/2000 | Rajaiah | ...................... | 523/120 |
| 6,102,050 A | 8/2000 | Marcon | ...................... | 132/321 |
| 6,475,498 B1 | 11/2002 | Rajaiah | ...................... | 424/401 |
| 6,677,391 B1 | 1/2004 | Rajaiah | ...................... | 523/120 |
| 6,905,672 B2 | 6/2005 | Rajaiah | ...................... | 424/49 |
| 7,563,096 B2 | 7/2009 | Goldiner | ...................... | 433/229 |
| 7,661,430 B2 | 2/2010 | Mason | ...................... | 128/848 |
| 8,070,710 B2 * | 12/2011 | Dougherty, Jr. | ...................... | 604/18 |
| 2006/0078694 A1 * | 4/2006 | Motoda et al. | ...................... | 428/32.24 |
| 2007/0110808 A1 * | 5/2007 | Bhattacharya et al. | ...................... | 424/473 |
| 2008/0200630 A1 | 8/2008 | Tanaka | ...................... | 526/319 |
| 2009/0137757 A1 | 5/2009 | Imuta | ...................... | 526/127 |
| 2011/0251417 A1 * | 10/2011 | Okawa | ...................... | 556/445 |

FOREIGN PATENT DOCUMENTS

| | | |
|---|---|---|
| JP | 2002-224144 | 8/2002 |
| JP | 2010-053775 | 3/2010 |
| JP | 2010-0523775 | 3/2010 |

OTHER PUBLICATIONS

Materials relating to EXAKTO-FORM (Material Safety Data Sheet and www page).
Materials relating to BREDENT (501(k) related materials).

* cited by examiner

*Primary Examiner* — James J Seidleck
*Assistant Examiner* — Peter A Salamon
(74) *Attorney, Agent, or Firm* — David R. Preston + Associates; David R. Preston

(57) ABSTRACT

The present invention includes a novel shapeable material or resin, specifically for dental use. It is an improvement over conventional dental resins because it is strong, safe, does not encourage the propagation of bacteria and contains no bisphenol A (BPA). Also, it is the preferred resiliency for use in the oral cavity.

24 Claims, 5 Drawing Sheets

| | The Product of This Invention | Polyamide | PET+ Polyethylene | Polycarbonate |
|---|---|---|---|---|
| Molding Temperature & Time | 200ºC - 210ºC  20 minutes | 210ºC - 220ºC  20 minutes | 240 ºC  20 minutes | 300ºC  25 minutes |
| Ease of compression | ◉ Extremely easy to compress | ◉ | ○ | ○ |
| Grinding feeling | Soft and can be whittled crisply | Cannot be whittled. | Slightly hard so can be whittled. | Hardest of all these and so it can be whittled. |
| Insertion and removal from plaster mold | Goes into the mold easily | Goes into the mold easily | Sticks fast in the mold. Is hard. | Sticks fast in the mold. Is hard. |
| Insertion and removal from plaster mold after moisture absorption | Not much different to before moisture absorption | Not much different to before moisture absorption | Not much different to before moisture absorption | Not much different to before moisture absorption |
| Repetitive bending test (before moisture absorption) | The part being bent turned white. | It tore after 47 times. | It tore after 14 times. | It broke after 5 times. |
| | No tears after 200 times | It broke after 129 times. | It broke after 38 times. | |
| Repetitive bending test (after moisture absorption) | The part being bent turned white | It tore after 53 times. | It tore after 12 times. | It broke after 6 times. |
| | No tears after 200 times | It broke after 118 times. | It broke after 51 times. | |
| Flexure Strength (MPa) | 61.2 | 59.5 | 72.2 | 91.0 |
| Elasticity (mm) | 12 or more | 12 or more | 12 or more | 12 or more |
| Hv Hardness | 9.8 | 9.4 | 11.3 | 13.2 |
| Moisture Absorption Rate (µg/mm3) | 0.13 wt% | 6 | 9 | 5 |
| Dissolution Rate (µg/mm3) | 0.1 wt% | 9.1 | 0.2 | 0.1 |
| Colour ΔE Curry | 1.29 | 31.29 | 5.84 | 0.96 |
| Colour ΔE Magenta | 5.18 | 24.8 | 21.96 | 10.88 |

FIGURE 1

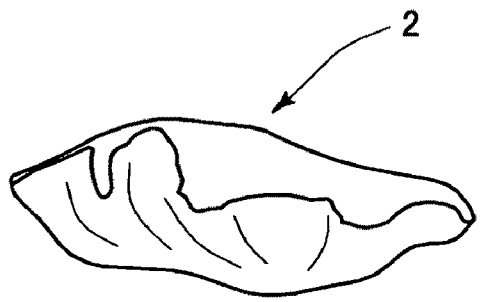
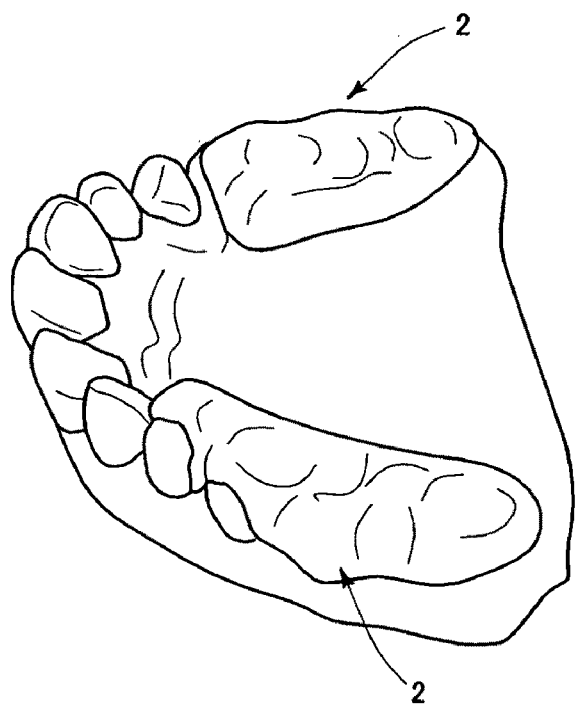
FIGURE 3

MOLDABLE RESIN FOR DENTAL USE

CROSS REFERENCE TO RELATED APPLICATIONS

This application claims benefit of priority to Japan patent No. 2010-053775 filed Mar. 10, 2010 the entire contents of which are incorporated herein by reference in its entirety.

TECHNICAL FIELD

The present invention generally relates to the field of shapeable materials and resins, specifically for dental use.

BACKGROUND

Strong, safe and moldable resins are essential materials for dentistry. Dental plates for dentures (false teeth), temporary crowns, artificial teeth and orthodontic devices are constructed from moldable dental resin. The resin is usually composed of acrylic or polycarbonate material.

Because these materials have high moisture contents, they create environments conducive to the propagation of saprophytic bacteria. With polycarbonate resins there is the additional problem of potential elusion of bisphenol A (BPA) which poses a safety concern. Other materials have been ineffective because of their low resistance to impact which causes them to break easily.

The present invention is an improvement over conventional dental resins because it is strong, safe, discourages the propagation of saprophytic bacteria and contains no BPA.

BRIEF DESCRIPTION OF THE FIGURES

FIG. 1 depicts a Table of results from a series of studies comparing the invention with traditional dental resins: Polyamide, PET+Polyethylene and Polycarbonate.

FIG. 3 depicts an orthodontic device for use to correct a patient's bite and the device fitted it in a patient's mouth.

SUMMARY

Figure 2:
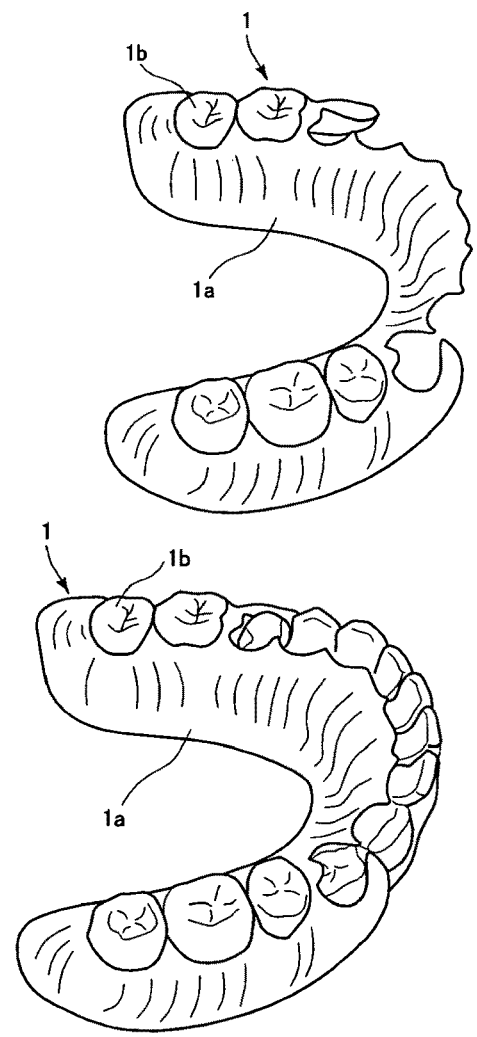
FIG. 2 depict a partial denture molded from the invention and the partial denture fitted into a patient's mouth.
Figure 4:
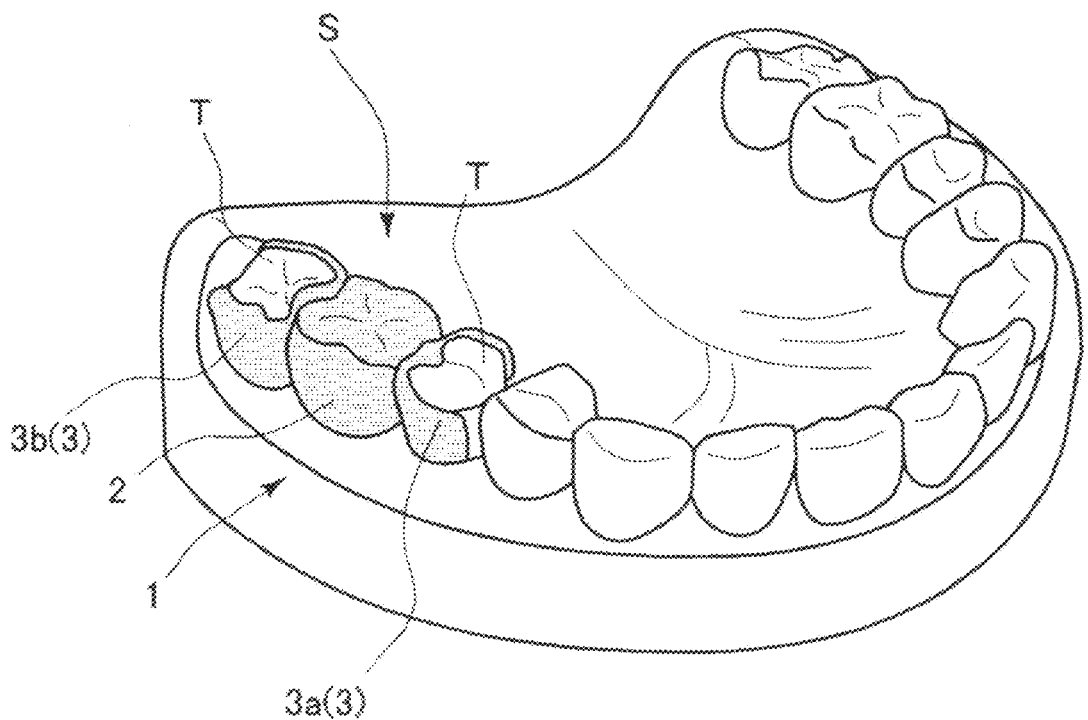
FIG. 4 depicts an orthodontic device for use to correct a patient's bite.
Figure 5:
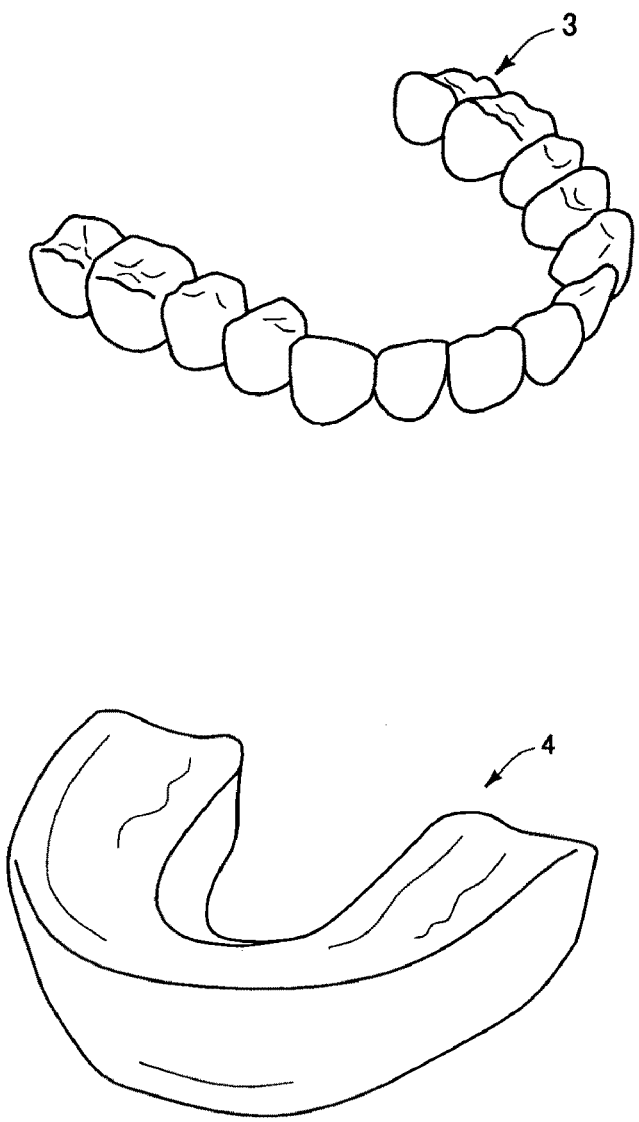
FIG. 5 depicts an example of artificial teeth molded from the invention and a mouthpiece molded from the invention.

The present invention includes a copolymer propylene moldable resin for dental use comprised of 65-90% polypropylene, 7-25% polyethylene or ethylene α-olefin copolymer, 0.01-2% magnesium stearate, 0.001-1% of either titanium oxide or iron oxide or both and 0.0001-1% color pigment.

In another aspect of the invention, a copolymer propylene moldable resin for dental is comprised of 75-85% polypropylene, 15-20% polyethylene or ethylene α-olefin copolymer, 0.03-0.5% magnesium stearate, 0.003-0.1% of either titanium oxide or iron oxide or both and 0.001-0.1% colour pigment.

The molded article for dental use may be used in denture plates, temporary crowns, artificial teeth and orthodontic devices.

Polypropylene and polyethylene (or ethylene α-olefin copolymer) in this range produces the ideal resin that is moldable for dental use. The product remains durable and will not flake, warp or expand. However, it is also the appropriate resiliency to be comfortably used in the human oral cavity. The magnesium stearate leads to a resin that is easily mixed with pigment. Moreover, color pigment in this range is ideal for uniform coloration of the product.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein are well known and commonly employed in the art. Where a term is provided in the singular, the inventors also contemplate the plural of that term. The nomenclature used herein and the procedures described below are those well known and commonly employed in the art.

"Principal component" means a component making up 90% or more of the content. 'Principal component' throughout this document has this meaning.

Introduction

Moldable resins are an essential component to materials used in modern dentistry. Dental plates for dentures (false teeth), temporary crowns, artificial teeth and orthodontic devices are composed of moldable dental resin. The resin must be strong with a high resistance to impact. It must also have the appropriate firmness and resiliency to be comfortable and effective in the oral cavity. Safety is also essential because humans may be exposed to the materials for long periods of time. Traditionally, dental professionals have relied on resin composed of acrylic or polycarbonate material. These materials present need for improvement.

Because traditional materials have high moisture contents, they create environments conducive to the propagation of saprophytic bacteria. This is of particular concern in the patient's mouth because of the ubiquitous nature of oral bacteria. With polycarbonate resins there is the additional problem of potential elusion of bisphenol A (BPA). BPA has been known to be estrogenic and presents safety concerns. Other synthetic materials may cause allergic reactions to patients.

The present invention is a safe, moldable resin for dental use which has a high structural strength. The physical properties of the invention make it particularly suitable for dental use. It is moldable and once shaped, is appropriately firm for use in the oral cavity. Moreover, unlike conventional acrylic resins and polycarbonate resins, it does not have a high moisture content. This discourages the propagation of saprophytic bacteria. It is antiallergenic as well as free from BPA.

A first aspect of the invention is a moldable resin that is shaped specifically for dental use for a patient's particular needs. The principal component of the resin is a copolymer polypropylene material comprising essentially of (by weight) 65-90% polypropylene, 7-25% polyethylene or ethylene α-olefin copolymer, 0.01-2% magnesium stearate, 0.001-1% of either titanium oxide or iron oxide or both, and 0.0001-1% color pigment.

The resin may be used for a myriad of dental devices including false teeth, temporary crowns, artificial teeth and orthodontic devices. Denture plates are generally colored pink to match the color of the gums. They serve to support artificial teeth for full and partial dentures. These include non-clasp dentures, which are the denture bases of dental plates that do not use wires or metal (called oral retainers or clasps), and denture bases of dental plates that do have wire clasps.

A second aspect of the invention is a moldable resin that is shaped specifically for dental use for a patient's particular needs. The principal component of the resin is a copolymer polypropylene material comprising essentially of (by weight) 75-85% polypropylene, 15-20% polyethylene or ethylene α-olefin copolymer, 0.03-0.5% magnesium stearate, 0.003-0.1% of either titanium oxide or iron oxide or both, and 0.001-0.1% color pigment.

Polypropylene and polyethylene (or ethylene α-olefin copolymer) in this range produces the preferred resin that is moldable for dental use. The product remains durable and will not flake, warp or expand. However, it is also the appropriate resiliency to be comfortably used in the human oral cavity. The magnesium stearate leads to a resin that is easily mixed with pigment. Moreover, color pigment in this range is ideal for uniform coloration of the product.

The resin may be used for a myriad of dental devices including false teeth, temporary crowns, artificial teeth and orthodontic devices. Denture plates are generally colored pink to match the color of the gums. They serve to support artificial teeth for full and partial dentures. These include non-clasp dentures, which are the denture bases of dental plates that do not use wires or metal (called oral retainers or clasps), and denture bases of dental plates that do have wire clasps.

Temporary crowns include mouth pieces, temporary teeth fitted after tooth removal and crowns (used to cover teeth following an implant procedure until the implant stabilizes) which are considered temporary. Artificial teeth include false teeth that are incorporated into the denture base and teeth that are implanted directly into the oral cavity. Orthodontic devices include intra-orally fitted appliances for correcting the bite of the upper and lower jaw, correcting the tooth bed and correcting tooth alignment and tooth angle.

For these types of materials, one usually colors (dyes) the denture plate pink to match the color of the gums. Red pigments are used along with titanium oxide to add whiteness. In the alternative, iron oxide may be added as a dulling additive to the red pigment. This allows one to create a color that closely resembles the actual color of the gums. The preferred method is to use titanium oxide and iron oxide together with the red pigment to obtain a color that most closely matches the gums.

For artificial teeth, one usually seeks a color midway between yellow and white. For this reason, a yellow pigment is used along with white titanium oxide. This leads to resin with a 'creamy' color that closely matches the natural color of teeth. For temporary crowns and orthodontic devices, it may not be essential to match them exactly to the color of the gums. But it is possible to color them to match the gums in the same way as denture bases. When temporary crowns and orthodontic devices are not made to match the gums, pigment of any desired color may be mixed with titanium oxide or iron oxide to make an appropriate color.

The resin material for fabricating (typically injection molding) molded articles for dental use such as those described above is available for use in such shapes as pellets, sheets and blocks as well as various other forms that make it easy to soften and mold the resin material.

Particular attention should be given to the makeup of the resin. Resin that contains less then 65% polypropylene is susceptible to flaking, warping and breaking. Resin with more than 90% polypropylene is incompatible with the oral cavity because of swelling of the article. Resin containing less than 7% polyethylene or ethylene α-olefin copolymer will also be susceptible to flaking, warping and breakage. Conversely with more than 25% polyethylene or ethylene α-olefin copolymer, problems may develop within the oral cavity incompatibility because of swelling of the article.

Particular attention should also be given to the ratio of magnesium stearate in the resin. It makes the resin easier to mix or blend with the pigment and titanium oxide (or iron oxide). If the weight ratio is less than 0.01% or more than 2%, it may be difficult to mix the pigment. As stated, with molded dental articles, the resin is stained pink in order to bring it closer to the color of the gums within the oral cavity. Pigments and titanium oxide (or iron oxide) are added to provide color and to bring out a color that is close to that of the actual gums (pink). When the ratio of titanium oxide is increased, the reddishness of the pink color is suppressed making a pink with a strong whitish tinge. Conversely, reducing the ratio of titanium oxide produces a pink with a strong reddish tinge. Iron oxide is added to the red pigment to lower the saturation and brightness of the red color, bringing it closer to the natural gum color. Both titanium oxide and iron oxide may be added together to stain the resin to a desired color.

Because of its relationship with the pigment, one determines the proper amount of titanium oxide (or iron oxide) content depending on the method of staining. The magnesium stearate aids in mixing the pigments. Titanium oxide (or iron oxide) with the resin may also help produce a uniform color throughout the resin. If the weight ratio of either the titanium oxide or iron oxide is less than 0.001%, it will not likely be effective. A higher concentration (more than 1%) may cause it to interfere with the strength and other physical properties of the resin material.

If the weight ratio of pigment is less than 0.0001%, coloration may be ineffective. Too much pigment (greater than 1%) may cause undesirable effects on the physical properties of the resin.

To produce the resin, isotactic polypropylene is dissolved between 180-220 degrees Celsius. Other components, according to the ratios discussed above, are then added. Magnesium Stearate and titanium dioxide increase the binding force of polymers at the molecular level. The binding state of copolymer molecules occurs during this dissolving and mixing process which contributes to the particular characteristics of the resin. One determines the amount of time needed for polymerization based on the volume.

Producing resin with these ranges of components leads to an improved material over traditional resins. The process of shaping the resin article as it cooled after injection molding was also easier. The resin could be fitted into the patient's mouth with great precision. The material maintains an ideal plasticity for this process. A different composition of materials would alter the flexural strength unique to this invention. Moreover, the shaping and subsequent use of the resin would be a challenge.

The invention is an improvement over other resins because it is more easily molded into desired shapes. In traditional resins, white fold lines may appear due to bending as the resin is shaped. Also, denture plates can warp and develop become brittle and the resin may swell after injection molding leading to a product that does not fit precisely into a patient's mouth. The user does not encounter these problems using the invention.

The invention also leads to a more user-friendly product. The material more easily slides in and out of the patient's mouth. For a removable device such as a denture, there is less resistance due to friction which makes it easier for the patient to take it in and out of his or her mouth.

Also, because moisture absorption is extremely low, propagation of saprophytic bacteria is suppressed. The resin is durable and has low specific gravity (lightweight) which makes it more comfortable to the patient. This allows patients to use such product more hygienically and comfortably over longer periods of time.

When constructing a molded article for dental use using the resin of this invention, the resin material is melted, and generally molded articles for dental use are molded by injection molding. As stated previously, this can provide denture bases, temporary crowns, artificial teeth orthodontic devices and other molded articles for dental use that are highly safe, cause no allergic reaction to resin in the human body and are free from elusion of bisphenol A.

As resin material for dental use, by weight ratio, with 80% polypropylene as the principle component, 18% ethylene α-olefin copolymer is co-polymerized to obtain a purified polypropylene. For this polypropylene, the blend is adjusted to a weight ratio of 80% polypropylene homopolymer $[CH_2-CH(CH_3)]m$, 18% ethylene-propylene copolymer $[CH_2-CH(CH_3)]m-[CH_2-CH_2]n$ as the ethylene α-olefin copolymer, and as additives, 0.1% magnesium stearate, 0.03% titanium oxide and 0.03% pigment (selecting one type of pigment from common dyes, aluminium lake or red iron oxide and other organic an inorganic pigments, or selecting several pigments and blending them for use). In place of titanium oxide, iron oxide can also be used in the same blend ratio, or both titanium oxide and iron oxide can be mixed to form a total weight of 0.03%. Also, as an ethylene α-olefin copolymer, besides ethylene propylene copolymer, for instance ethylene-butene may be used. Furthermore instead of ethylene α-olefin copolymer, one could use about 18% of polyethylene.

It should be noted that substances apart from those mentioned above may be present as inevitable impurities or as additives for a prescribed purpose within the range of 2% or less. However, low levels of impurities may not affect the quality of the product.

One may use common molding equipment to fabricate denture plates, orthodontic devices, dentures, or temporary crowns. The invention is compatible with common molding equipment and routine methods such as injection molding, compression molding or vacuum pressurization that are commonly used by dental practitioners in the art. When fabricating the molded articles for dental use using injection molding, the resin material of this invention is generally used in the raw material from pellets. The pellets are placed into the barrel of a general-use resin molding machine, softened and melted at a furnace temperature setting of between 180° C. and 230° C. before performing the injection molding. With this invention, since magnesium stearate is mixed in as an additive. It has high fluidity which makes it possible to precisely reproduce the molded article along with very fine details.

The present invention offers the following improvements over traditional dental resins.
1. The resin is antiallergenic.
2. It does not contain bisphenol A (BPA).
3. It is free from other additives that may elute from traditional resins.
4. It is conducive to the use of polyester fibers that may be dyed the color of the blood vessels in the oral cavity and embedded into the molded article.
5. The use of magnesium stearate improves staining and the allows it to more accurately mimic the color of natural gums.
6. The use of magnesium stearate improves the surface gloss of the resin since makes the denture plate can more easily inserted and removed.
7. The use of titanium oxide (iron oxide) improves staining of the denture plate and makes it possible to accurately mimic the natural shade of human gums.
8. The resin has superior mechanical strength, flexural strength and heat resistance, compared to traditional dental
9. Because the resin is less moisture absorbent than conventional resin materials, there is less propagation of bacteria and less resin deterioration.
10. The resin has a lighter specific gravity than traditional resins which decreases the burden placed on tissues within the oral cavity.
11. Because the resin is less moisture absorbent than conventional resin materials, it is effectively stored at room temperature, and there is no need to heat-dry it to remove moisture during injection molding. This makes production of dental materials with the resin more efficient.

Evaluation testing was performed on an article molded from the resin molding of this invention as described above. The results are set out in FIG. 1.

This aspect of the invention, as well as others described herein, is achieved by using the methods, articles of manufacture and compositions of matter described herein. To gain a full appreciation of the scope of the present invention, it will be further recognized that various aspects of the present invention can be combined to make desirable embodiments of the invention.

DESCRIPTION OF THE PREFERRED EMBODIMENT

Because other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

EXAMPLES

Example 1

In the repetitive bending test when measurements were taken before and after moisture absorption, with this invention better results were obtained both times than for other resin materials for dental use. For example, in the repetitive bending test before absorption, the polycarbonate broke after 5 times, the polyethylene terephthalate (PET)+polyethylene compound resin tore after 14 times and broke after 38 times, the polyamide tore after 48 times and broke after 129 times, but with this invention the part being bent only became white and did not tear or fracture even after bending 200 times.

Also, in the repetitive bending test after moisture absorption, the polycarbonate broke after 6 times, the PET+polyethylene tore after 12 times and broke after 51 times, the polyamide tore after 53 times and broke after 118 times, but with this invention the part being bent only became white and was still untorn after bending 200 times. The flexural strength of the resin material (molded article) of this invention was 61.2 Mpa, elasticity was 12 mm or more, absorption rate 0.13 wt %, and dissolution rate 0.1 wt %, all of which were good results. Apart from this, as shown in the attachment good results were also obtained in workability and coloration tests.

Example 2

As supplementary information about the coloration test, the second line from the bottom of Table 1 'Color ΔE Curry' means that the resin test piece was placed in a mixture of curry powder dissolved in hot water and left for 1 week at 37° C., after which the resin test piece was removed and tested using a special testing device to see how much it had been colored by the curry powder, and the test results were expressed in numerical form. The smaller the number, the lesser the degree of coloration, in other words there is less discoloration. Also, 'Color ΔE Magenta' indicates a similar test conducted using magenta instead of curry powder, and the smaller the number, the less discoloration was observed. As is clear from these results, with this invention, the test result was 1.29 for 'Color ΔE Curry' and 5.19 for 'Color ΔE Magenta', which were sufficiently smaller than the values for polyamide and PET+ polyethylene, indicating that it does not discolor easily.

Example 3

Furthermore, a heat resistance test was conducted in the following way. The resin material of this invention was made and modified into a sheet measuring 20 mm×20 mm×3 mm in size by injection molding, then left steeping in boiling water (approx. 100° C.) for 1 hour, and when the external appearance of the molded article was examined, no surface roughness or clouding was observed. Therefore, similar results can be obtained for denture plates, temporary crowns, orthodontic devices and artificial teeth etc made with the material of this invention.

EXPLANATION OF NUMERATION

1 Denture
1 a Denture Plate
1 b Artificial Teeth
2 Orthodontic Device
3 Artificial Teeth
4 Mouthpiece (Temporary Crown)

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A copolymer propylene moldable resin in a dental device, comprising:
   a) between 65% and 90% polypropylene;
   b) between 7% and 25% polyethylene or ethylene α-olefin copolymer, either alone or in combination;
   c) between 0.01% and 2% magnesium stearate;
   d) between 0.001% and 1% of titanium oxide or iron oxide, either alone or in combination; and
   e) between 0.0001% and 1% of color pigment;
   wherein said copolymer propylene moldable resin is provided in an intra-oral dental device selected from the group consisting of a denture plate, a temporary crown, a crown, an artificial tooth, a mouthpiece, and an orthodontic device.

2. The copolymer propylene moldable resin of claim 1, wherein said intra-oral dental device is a denture plate.

3. The copolymer propylene moldable resin of claim 1, wherein said intra-oral dental device is a temporary crown.

4. The copolymer propylene moldable resin of claim 1, wherein said intra-oral dental device is a crown.

5. The copolymer propylene moldable resin of claim 1, wherein said intra-oral dental device is an artificial tooth.

6. The copolymer propylene moldable resin of claim 1, wherein said intra-oral dental device is a mouthpiece.

7. The copolymer propylene moldable able resin of claim 1, wherein said intra-oral dental device is an orthodontic device.

8. The copolymer propylene moldable resin of claim 1, comprising between 75% and 85% polypropylene.

9. The copolymer propylene moldable resin of claim 1, comprising between 15% and 20% polyethylene or ethylene α-olefin copolymer, either alone or in combination.

10. The copolymer propylene moldable resin of claim 1, comprising between 0.03% and 0.5% magnesium stearate.

11. The copolymer propylene moldable resin of claim 1, comprising between 0.003% and 0.1% titanium oxide or iron oxide, either alone or in combination.

12. The copolymer propylene moldable resin of claim 1, comprising between 0.001% and 0.1% color pigment.

13. An intra-oral dental device comprising the copolymer propylene moldable resin of claim 1, wherein said intra-oral dental device is selected from the group consisting of a denture plate, a temporary crown, a crown, an artificial tooth, a mouthpiece, and an orthodontic device.

14. The intra-oral dental device of claim 13, wherein said intra-oral dental device is a denture plate.

15. The intra-oral dental device of claim 13, wherein said intra-oral dental device is a temporary crown.

16. The intra-oral dental device of claim 13, wherein said intra-oral dental device is a crown.

17. The intra-oral dental device of claim 13, wherein said dental device is an artificial tooth.

18. The intra-oral dental device of claim 13, wherein said intra-oral dental device is a mouthpiece.

19. The intra-oral dental device of claim 13, wherein said intra-oral dental device is an orthodontic device.

20. The intra-oral dental device of claim 13, comprising between 75% and 85% polypropylene.

21. The intra-oral dental device of claim 13, comprising between 15% and 20% polyethylene or ethylene α-olefin copolymer, either alone or in combination.

22. The intra-oral dental device of claim 13, comprising between 0.03% and 0.5% magnesium stearate.

23. The intra-oral dental device of claim 13, comprising between 0.003% and 0.1% titanium oxide or iron oxide, either alone or in combination.

24. The intra-oral dental device of claim 13, comprising between 0.001% and 0.1% color pigment.

* * * * *